United States Patent

[19] Holmes

[11] 4,035,389
[45] July 12, 1977

[54] PRODUCTION OF 2,2-DISUBSTITUTED PROPIOLACTONES

[75] Inventor: Jerry D. Holmes, Longview, Tex.

[73] Assignee: Eastman Kodak Company, Rochester, N.Y.

[21] Appl. No.: 648,080

[22] Filed: Jan. 12, 1976

Related U.S. Application Data

[60] Continuation-in-part of Ser. No. 609,881, Sept. 2, 1975, which is a division of Ser. No. 491,092, July 23, 1974, Pat. No. 3,931,237, which is a continuation-in-part of Ser. No. 394,370, Sept. 4, 1973, abandoned.

[51] Int. Cl.$^2$ .................................... C07D 305/12
[52] U.S. Cl. .......................... 260/343.9; 252/456
[58] Field of Search ............................. 260/343.9

[56] References Cited

U.S. PATENT DOCUMENTS 3,907,829  9/1975  Holmes et al. ............... 260/343.9
3,915,995  10/1975  Holmes et al. ............... 260/343.9

Primary Examiner—Cecilia M. S. Jaisle
Attorney, Agent, or Firm—Edward R. Weber; Daniel B. Reece, III

[57] ABSTRACT

The present invention relates to a process for the manufacture of 2,2-disubstituted propiolactones from isoanhydrides and formaldehyde, as shown in the following equation:

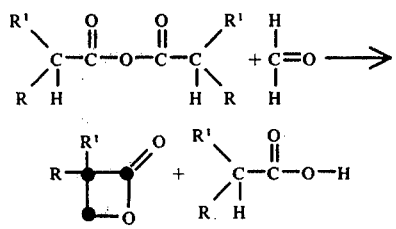

wherein R and R$^1$ individually may be a straight- or branched-chain alkyl, aryl or aralkyl group having 1 to 10 carbon atoms. The reaction is conducted at a temperature of from about 190° C. to about 400° C. in the presence of the metal oxide-silica gel complex which results from heating the calcined residue of a salt of a metal selected from the group consisting of Ta, Ti, Nb and Zr supported upon a silica gel in the presence of nitrogen and steam at a temperature of from about 650° C. to about 1000° C. which complex has additionally been treated by soaking in a mineral acid at a temperature of from about 25° C. to about 100° C. for from about 1 to about 4 hours.

30 Claims, No Drawings

PRODUCTION OF 2,2-DISUBSTITUTED PROPIOLACTONES

This is a continuation-in-part of my copending application Ser. No. 609,881 filed Sept. 2, 1975, which application is a divisional application of application Ser. No. 491,092 filed July 23, 1974, entitled "Production of 2,2-Disubstituted Propiolactones" now U.S. Pat. No. 3,931,237 which application was in turn a continuation-in-part of application Ser. No. 394,370 filed Sept. 4, 1973, now abandoned.

The present invention relates to a process for preparing 2,2-disubstituted propiolactones by the reaction of an isoanhydride with formaldehyde according to the following formula:

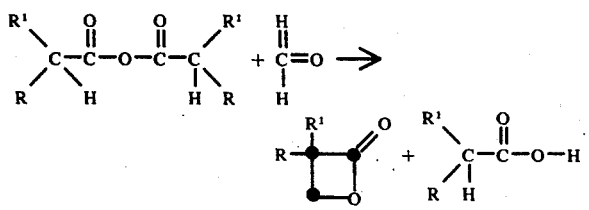

wherein R and $R^1$ individually may be a straight- or branched-chain alkyl, aryl, or aralkyl group having 1 to 10 carbon atoms, preferably 1 to 6 carbon atoms, at a temperature of from about 190° C. to about 400° C.

2,2-Disubstituted propiolactones are useful in the polymer industry as a starting material for synthetic resins and synthetic fibers. They are also useful in the pharmaceutical industry and have heretofore been prepared by a variety of methods. For example, in U.S. Pat. No. 2,356,459, there is described a well-known method for preparing 2,2-disubstituted propiolactones by the addition reaction of dimethyl ketene and formaldehyde. The known methods for the manufacture of 2,2-disubstituted propiolactones, however, can be practiced on a commercial scale only with difficulties and resultant economic disadvantages.

It is, therefore, an object of my invention to provide a simplified method for the preparation of 2,2-disubstituted propiolactones.

It is another object to provide a one-step method for the preparation of 2,2-disubstituted propiolactones.

Yet another objective is to provide an improved catalyst having longer life and which catalyst can be readily restored to its initial activity.

Other objects of the invention will become apparent from a consideration of the specification and claims of this application.

The prior literature described a reaction of primarily aromatic aldehydes with anhydrides to give unsaturated acids. These reactions are normally conducted in the liquid phase using basic catalysts. Aliphatic aldehydes are usually unsuitable for this reaction. In the liquid phase, aldehydes normally react with anhydrides to form gem-diesters. For example, formaldehyde, when reacted with butyric anhydride, normally gives methylene dibutyrate (J. F. Walker, "Formaldehyde", 3rd Ed., ACS Monograph Series No. 152, Reinholt, p. 350). No prior literature is known which describes the condensation of aldehydes with acid anhydrides to produce lactones. U.S. patent application Ser. No. 303,567 filed Nov. 3, 1972, discloses a process for producing 2,2-disubstituted propiolactones from an isoanhydride and formaldehyde in the presence of a catalyst consisting of a supported heavy metal oxide. These catalysts, however, are not completely satisfactory because they give substantially lower yields and conversions to the desired lactone or they lose activity during use and are difficult to reactivate.

In the process of the instant invention, an isoanhydride having the formula

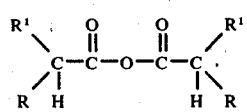

is condensed with formaldehyde to yield a 2,2-disubstituted propiolactone having the formula

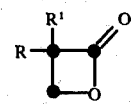

and an organic acid having the formula

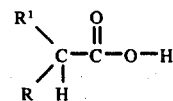

wherein R and $R_1$ individually may be a straight- or branched-chain alkyl, aryl or aralkyl group having 1 to 10 carbon atoms, preferably 1 to 6 carbon atoms. The reaction is catalyzed by the acid treated metal-oxide silica gel complex which results from heating the calcined residue of silica gel and a water-soluble salt of a metal selected from the group consisting of tantalum, titanium, niobium and zirconium in the presence of nitrogen and steam at a temperature of from about 650° C. to about 1000° C. and preferably less than about 900° C. which complex has been additionally treated by soaking in a mineral acid such as HCl, HF, HBr, $HNO_3$, $H_2SO_4$, or $H_3PO_4$.

Good results are obtained when the calcined residue is heated at a temperature of from about 730° C. to about 780° C. for a period of from about 3 to about 6 hours. Following this steam treatment the catalyst is cooled and soaked in dilute HCl, approximately 5%, for about 2 hours using temperatures of from about 25° C. to about 100° C.

These catalysts give almost complete reaction of formaldehyde with isobutyric anhydride to form pivalolactone and, to a minor degree, a secondary reaction product, isobutyroxypivalic anhydride. The by-product appears to be formed from the secondary reaction of pivalolactone with isobutyric acid to form isobutyroxypivalic acid, which then interchanges with excess isobutyric anhydride as shown below.

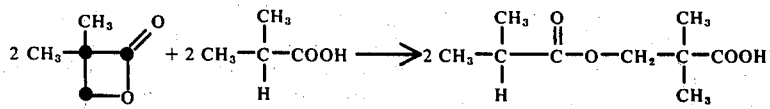

-continued

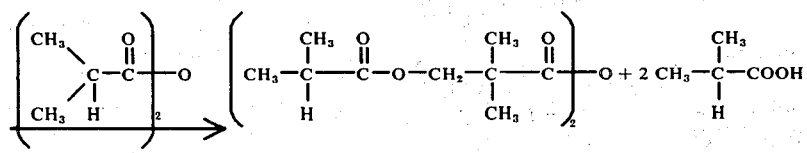

The by-product isobutyroxypivalic anhydride (hereinafter designated as IBPVA) is useful since it may be converted to pivalolactone by a separate step. Formaldehyde in the instant reaction may not be readily recovered. It is therefore desirable that conversion of formaldehyde to the useful products pivalolactone and/or IBPVA be as high as possible.

A common method of catalyst regeneration is to burn carbonaceous material from the catalyst at temperatures of up to about 550° C. The 550° C. temperature is selected since above about 600° C. silica gel begins to sinter and lose its structural properties. Since it had been determined that heating at 550° C. had very little effect on the catalyst activity of a heavy metal oxide catalyst, it was quite surprising that heating a heavy metal oxide-silica gel catalyst to temperatures of from about 650° C. to about 1000° C. in the presence of steam produced a highly selective catalyst with long life which could be readily regenerated.

Likewise, it was quite surprising that certain acid treatments could be used to impart additional catalyst activity and/or selectivity. One would normally predict that mineral acids absorbed on a support such as silica gel would rapidly lose activity because of the tendency to leach the acid from the support. In the instant invention the acid apparently interacts with the metal oxide and/or silica gel to form a stable species since increased catalyst life is one of the results of the acid treatment.

The supported metal oxide catalysts of the instant invention are conveniently formed by mixing one of their water-soluble salts such as a nitrate, acetate, oxalate, or ammonium salt with a silica gel and then removing the water by evaporation. Calcining the material in nitrogen at from about 400° C. to about 600° C. and then in air at from about 400° C. to about 600° C. produces the desired silica gel supported metal oxide. A preferred temperature range for the calcining step is from about 500° C. to about 550° C. If desired, the metal oxide can be precipitated directly upon the support by use of a suitable chemical reaction. A relatively low surface area (340 square meters per gram) and large pore volume (1.15 cc. per gram) silica gel has been found to be particularly effective.

The silica gel supported calcined metal oxide is then heated in a nitrogen steam mixture at a temperature of from about 650° C. to about 1000° C. until the desired metal oxide silica gel complex is formed, usually from about 2 to about 10 hours. The nitrogen is used to facilitate more uniform heat distribution. Good results have been obtained with $N_2$ to $H_2O$ ratios of from about 0.1:1 to about 10:1.

During the heat treating cycle the relationship of time of treatment to temperature may be varied considerably. Higher temperatures require shorter treatment times and vice versa. An excellent catalyst has been obtained by steam treatment in nitrogen at 760°–780° C. for 4 to 6 hours. It is essential, however, that the steam treatment be in the 650°–1000° C. range. A more practical measurement to obtain a catalyst of greater activity, selectivity and life span is based on the volume of the solid catalyst. When the catalyst being treated at 650°–1000° C. has been reduced in volume by not less than 5 percent and not more than 20 percent, the desired catalyst complex has been attained.

The importance of treatment at 650°–1000° C. is further described as follows. If insufficient heat treatment is used, the catalyst is too active and produces considerable decomposition resulting in low conversions and yields to lactones. On the other hand, if too much heat is applied the catalyst begins to lose activity which results in low conversions and a short lifetime.

Following the aforementioned heat treating, the catalyst is allowed to cool and is then soaked in a mineral acid. Mineral acids which have been found useful include HCl, HF, HBr, $HNO_3$, $H_2SO_4$ and $H_3PO_4$. The temperature used and the time of soaking depend primarily on the acid strength and concentration. The effectiveness of the treatment also depends on the type and strength of the acid. For example, HCl proved to be very effective whereas phosphoric acid gave only a small degree of improvement in catalyst efficiency. Other acids fall in between these two extremes.

An exact description of the catalyst complex is not available. It is best characterized by the unique, greatly improved properties it exhibits when compared to analogous catalyst or those prepared by alternate methods.

In a preferred embodiment of the subject invention an aqueous solution of tantalum oxalate is used as a convenient source of soluble tantalum for the deposition oxide of tantalum oxide on the silica gel. The catalyst is prepared by soaking the silica gel in an aqueous solution of the tantalum oxalate, removing the water by evaporation, calcining the solid residue in nitrogen at a temperature of about 550° C. for 1½ hours and then in air at a temperature of about 550° C. for 1½ hours, and heating the resultant silica gel-tantalum oxide mix in a nitrogen steam mixture at a temperature of from about 650° C. to about 1000° C. for 2 to 8 hours. The heat treated catalyst is then cooled and soaked in a solution of dilute HCl (approximately 5%) for about 2 hours at a temperature of between about 25° C. and about 100° C. A lower temperature is normally preferred since higher temperatures can produce excessive acidification and somewhat reduce catalyst selectivity. A higher temperature however will normally produce a slight increase in catalyst life.

Acid treatment of freshly prepared metal oxide silica gel catalyst as described above greatly increases the effective life of the catalyst. The overall catalyst activity is also increased. This is shown by an increase in formaldehyde conversion to be disubstituted propiolactone and products derived from the disubstituted propiolactone.

Equally important, the acid treatment provides a very good method for reactivating the catalyst after it has lost activity from repeated use. Simple burning of the catalyst to a clean state with air, as is normally done, does not completely restore the catalyst activity. Burning the catalyst clean in the presence of steam at 550°

C. produces a significant improvement in regeneration although after the second regeneration higher concentrations of unreacted formaldehyde are noted in the reaction effluent. Acid treatment as described herein restores the activity of the catalyst. The acid treatment for regeneration is most effectively carried out by burning the catalyst clean of any carbonaceous deposits, cooling it and soaking it in a dilute aqueous solution of the desired mineral acid. Temperatures of from ambient to slightly less than 100° can be used. As in the treatment of fresh catalyst, the most desirable temperature will depend on acid type, strength and time of treatment.

Optimum process conditions such as contact time, temperature, amount of diluent gas and feed composition will vary for the different acid treated metal oxide-silica gel complex catalysts. In general, the best results are obtained at a contact time of from about 0.5 to about 2.5 seconds, although this may vary over a much broader range, such as from about 0.1 second to about 5.0 seconds.

Preferably the temperature selected will be sufficient to insure vaporization of the reactants and the products. The process may be operated at temperatures of from about 190° C. to about 400° C. A preferred temperature range is from about 240° C. to about 350° C.

Suitable anhydrides include isobutyric, 2-ethylhexanoic, 2-phenylpropionic, 2-ethylpropionic, 2-ethylbutyric, and 2-methylpentanoic.

Formaldehyde may be fed as a gaseous monomer, as a trioxane solution, or as a paraformaldehyde slurry. It has been found that the formaldehyde conversion to lactone is dependent on the amount of anhydride fed. A molar ratio of from about 1.15:1 to about 5:1, preferably from about 3:1 to about 4:1, of anhydride to formaldehyde (as trioxane) in the feed mixture produces good results. The optimum ratio will depend upon various manufacturing considerations, such as refining and recycling of unreacted feed materials. There appears to be no upper limit to this ratio other than practical manufacturing considerations which arise when a large excess of one material is introduced into a system. In general, a higher anhydride to formaldehyde ratio gives higher formaldehyde conversion, but also decreases the percentage of lactone in the product.

The reaction may be carried out at atmospheric, subatmospheric, or superatmospheric pressure. If desired, an inert diluent gas may be utilized to facilitate feeding of the reactants, control of contact time, etc. Good results are obtained at atmospheric pressure using an inert diluent gas, usually in a molar ratio of gas to organic feed of from about 1:10 to about 20:1, preferably about 1:1 to 6:1, and most preferably from about 2:1 to 4:1. A suitable inert diluent gas is any gas, such as $N_2$, argon, helium, gaseous hydrocarbons and compounds which are readily vaporized such as benzene, which does not react with either the reactants or the products under the conditions of the reaction.

The process of the invention is illustrated in greater detail by the following examples, which are all conducted at atmospheric pressure, but it will be understood that these examples are not intended to limit the invention in any way, and obvious modifications will occur to those skilled in the art.

EXAMPLE 1

This example illustrates the effectiveness of an acid treatment for imparting additional catalyst life by reactivating a used catalyst.

To a 600 milliliter beaker are charged 60 milliliters of tantalum oxalate solution (10.32 grams as tantalum or 12.6 grams as tantalum oxide) and 240 milliliters water. To this are added 100 grams Davison G-59, 7-10 mesh silica gel and the mixture is left standing overnight. The mixture is transferred to a large evaporating dish and taken to dryness on a steam bath. A small amount of powder is removed by collecting the catalyst on a 20 mesh screen.

To a conventional Vycor reactor (30 millimeters by 2 feet) are charged 36 milliliters of Vycor chips, 150 milliliters (99 grams) of the above catalyst and 100 milliliters of Vycor chips for preheat. The reactor is brought to 550° C. and nitrogen is fed at 8.18 moles per hour for approximately 1.5 hours. Air at 8.18 moles per hour is then substituted for the nitrogen for an additional 1.5 hours. At this time the air is shut off and nitrogen at 8.18 moles per hour is again started. Water feeding is started through a preheater (approximately 100° C.) at a rate of about 180 milliliters per hour and the temperature is rapidly brought to 760°–780° C. and held for six hours. After the heat is shut off, steaming is continued until the reactor temperature decreases to about 550° C. at which point water feeding is discontinued. After cooling, the catalyst is removed from the reactor and has lost 14 percent of its original volume to a final volume of 129 milliliters (60.4 grams).

The following procedure is followed for the generation by acid treatment of a deactivated catalyst.

The deactivated catalyst (50 milliliters) is burned clean by feeding $N_2$ at 3.5 moles per hour and air at 0.5 mole per hour while feeding water through a preheater at approximately 60 milliliters per hour. The temperature is increased to 550° C. and these conditions are held for 15–30 minutes. At this point the $N_2$ is decreased to 3 moles per hour and air increased to 1 mole per hour for approximately 30 minutes. Then 2 moles per hour of each is fed for 30 minutes and finally only air (4 moles per hour) and steam are fed for 1.5 hours. The catalyst is clean of carbon but has a slight yellow discoloration while hot. It is almost white when cooled in $N_2$.

The water and air feed are stopped and the catalyst is cooled in $N_2$ to 25°–35° C. After stoppering the bottom of the reactor, it is filled (approximately 130 milliliters) with 5.5 percent HCl (25 milliliters concentrated HCl and 175 milliliters $H_2O$) and allowed to stand at ambient temperature for two hours. The HCl is drained and the catalyst washed portionwise with a total of 400 milliliters of water. The reactor is put back under $N_2$ and dried by heating to reaction temperature and then put in service at the usual operating conditions.

The general procedure followed for testing all catalysts is described here. The reactor used is a 22 millimeter by 2 foot Vycor tube heated with a three-element furnace and charged with 35 milliliters Vycor chips, 50 milliliters catalyst and 90 milliliters Vycor chips for preheat. A nitrogen purge of 1.25 moles per hour is used and the reactant feed rate is held at 60–61 milliliters per hour. The operating temperature is controlled at 256°–266° C. and a 3 to 1 molar ratio of isobutyric anhydride to formaldehyde (fed as trioxane) is used as feed. Gas liquid chromatograph (4 foot 20 M TPA Carobwax column) is used to analyze the reaction product. A composite sample for each run is stripped at approximately 140° C. at 1–2 millimeters to determine percent high boilers which are used to correct chromatographic results.

Following this procedure 50 milliliters of the fresh catalyst without acid treatment are tested in continuous operation. Each run is made for a varying number of days and the results obtained with fresh catalyst, with catalyst after air and steam regeneration, and with catalyst after air and steam regeneration plus acid regeneration are summarized in Table I.

Total formaldehyde conversion to pivalolactone (PVL) and isobutyroxypivalic anhydride (IBPVA) is a direct measure of the catalyst activity and life. As shown in Table I fresh catalyst (Run 1) and catalyst burned clean with air and steam (Run 2) run only three days with a total formaldehyde conversion to PVL and IBPVA of 80 percent or better. The same catalyst burned clean with steam and air and then acid regnerated (Run 3) as described above runs eight days at an 80 percent or better total formaldehyde conversion. A similar increase in catalyst life is also illustrated by formaldehyde conversion to pivalolactone. Runs 1 and 2 run for three and four days, respectively, at a 70 percent or better conversion. Formaldehyde conversion to PVL is still 71 percent after 10 days using the acid regenerated catalyst as shown in Run 3.

Isobutyric anhydride yields to pivalolactone and isobutyroxypivalic anhydride are similar in all three runs. This illustrates that acid treatment of the catalyst (Run 3) is not detrimental to catalyst selectivity.

Run 3 in Table I clearly demonstrates the effectiveness of acid treatment for reactivating the catalyst and for imparting a substantial increase in the length of time the catalyst retains a high activity. After Run 3 the catalyst activity and life may be restored again by repeating the procedures used for Run 3.

EXAMPLE 2

This example illustrates the effectiveness of an HCl treatment for improving the useful lifetime of a freshly prepared catalyst.

A 500 milliliter portion of a nominal 10 percent tantalum (as the oxide) on Davison G-59 silica gel which has been calcined at 550° C. with nitrogen, air and the nitrogen again is charged to a Vycor tubular reactor and heated to 750° ± 10° C. in the presence of a flow of air at 500 milliliters per minute and water at 300 milliliters per hour for two hours. After cooling, the recovered catalyst exhibits a 5 percent loss in volume. This is referred to as the steam treated catalyst.

A 50 milliliter portion of this steam treated catalyst contained in a tubular reactor is heated to 250°–265° C. in a nitrogen flow of 465 cc per minute and a solution of trioxane in isobutyric anhydride (1:3 on a molar basis) is vaporized and passed over the catalyst at a rate of about 57 milliliters of liquid feed per hour. The results of the run are summarized in Table II (Run 1).

A 70 milliliter portion of the fresh steam treated catalyst is covered with 140 milliliters of 1.5 N aqueous hydrochloric acid and held at ambient temperatures for 2 hours. The excess liquid is decanted from the solid residue, and the solid granules are washed by decantation with four 140 milliliter portions of water and finally dried on a steam bath.

A 50 milliliter portion of this acid treated catalyst is placed in the previously described tubular reactor and heated to 250°–265° C. in a nitrogen flow of 465 cc. per minute. A solution of trioxane in isobutyric anhydride (1:3 on a molar basis) is vaporized and passed over the catalyst at a rate of about 64 milliliters of liquid feed per hour. The results of this run are also summarized in Table II (Run 2).

It can be seen that the effective lifetime of the catalyst is extended as indicated by the total formaldehyde conversion.

The hours of operation wherein a formaldehyde conversion of 79 percent or better are extended to 79 (Run 2). This compares to 59 hours of operation to the 79 percent formaldehyde conversion without acid treatment (Run 1).

The selectivity of pivalolactone remains essentially unchanged.

EXAMPLE 3

This example illustrates the ineffectiveness of treating the silica gel support alone with hydrochloric acid. The reactor as described in Example 1 is charged with 50 milliliters Davison G-59 silica gel, stoppered and filled with a mixture of 175 milliliters water and 25 milliliters concentrated hydrochloric acid. This is heated at 80°–95° C. for 2 hours. The reactor is then drained and the silica gel washed portionwise with 400 milliliters of distilled water. The catalyst is then dried by heating to 100°–150° C. for 0.5 to 1.0 hour with a nitrogen purge.

A typical run is then made at 255°–265° C. feeding a 3:1 mixture of isobutyric anhydride to trioxane.

The pivalolactone concentration falls from an initial value of 4.6 to 2.6 percent after 5 hours. For the five hour period formaldehyde conversion to pivalolactone is 16 percent and the isobutyric anhydride yield to pivalolactone is 47 percent.

EXAMPLE 4

This example illustrates the effectiveness of treatments with phosphoric acid, both at ambient temperatures and when warmed, in promoting the activity of the catalyst and in extending its effective lifetime.

A 45 milliliter porton of a steam treated catalyst contained in a typical tubular reactor is heated to 250°–265° C. in a nitrogen flow of 200 milliliters per minute and a solution of trioxane in isobutyric anhydride (1:3 on a molar basis) is vaporized and passed over a typical steam-treated tantalum oxide-silica gel catalyst at a rate of about 58 milliliters of liquid feed per hour. The results of the run are summarized in Table III (Run 1). After the run is completed, the catalyst is burned clean at 550° C. by gradually replacing a nitrogen stream with air and steam. Full air and steam are passed through the hot bed (550° C.) until the carbon deposits are removed and the catalyst bed appears clean visually. The catalyst is then cooled to ambient temperature under nitrogen.

The cleaned catalyst is held in contact with 1.5 N phosphoric acid for two hours at ambient temperature, washed with four 100 milliliter portions of water and dried at 200° C. in air.

When a feed the same as in the previous run is fed over the catalyst at 255°–265° C. at a rate of about 65 milliliters of liquid feed per hour and with a nitrogen flow of 200 milliliters per minute, the results shown in Table III (Run 2) are obtained.

After a second steam-air cleaning, the catalyst is treated with 1.5 N phosphoric acid at 80°–100° C. for two hours. After washing and drying, the catalyst is heated to 250°-265° C. and the vaporized feed is fed at the rate of about 61 milliliters of liquid feed per hour with a nitrogen flow of 465 milliliters per minute. The results are summarized in Table III (Run 3).

As shown in Table III, total formaldehyde conversion to PVL and IBPVA drops to 51 percent after 23 hours using untreated catalyst (Run 1) but is still 62 percent after 28 hours when ambient temperature acid treatment with phosphoric acid is used (Run 2). When heat is used during the phosphoric acid treatment (Run 3), the total formaldehyde conversion is still 57 percent after 70 hours.

at 50°-60° C., washed with four 200 milliliter portions of water, and dried at 260° C. in nitrogen.

The same feed composition as in Run 1 is vaporized and fed over the catalyst at 250°-265° C. at a rate of about 60 milliliters of liquid feed per hour and with a nitrogen flow of 465 milliliters per minute. The results are shown in Table IV (Run 3).

Total formaldehyde conversion to PVL and IBPVA is 73 percent after three days using the catalyst with no acid treatment (Run 1). Treating the catalyst with nitric acid as described gave 81 percent (Run 2) or 84 percent (Run 3) total formaldehyde conversion after 3 days. In either case, the isobutyric anhyride yield remained relatively unaffected at about 90 percent.

TABLE I

| Run No. | Days of Operation | CH$_2$O Conversion to | | | IBA Yield to | | |
|---|---|---|---|---|---|---|---|
| | | PVL (%) | IBPVA (%) | Total (%) | PVL (%) | IBPVA (%) | Total (%) |
| 1[1] | 1 | 65 | 21 | 86 | 58 | 28 | 86 |
| 1 | 2 | 69 | 15 | 84 | 65 | 22 | 87 |
| 1 | 3 | 70 | 11 | 81 | 70 | 17 | 87 |
| 1 | 4 | 68 | 9 | 77 | 70 | 15 | 85 |
| 2[2] | 1 | 74 | 12 | 86 | 70 | 17 | 87 |
| 2 | 2 | 76 | 7 | 83 | 76 | 11 | 87 |
| 2 | 3 | 74 | 6 | 80 | 80 | 9 | 89 |
| 2 | 4 | 71 | 6 | 77 | 78 | 9 | 87 |
| 2 | 5 | 69 | 6 | 75 | 79 | 11 | 90 |
| 2 | 6 | 67 | 5 | 72 | 78 | 9 | 87 |
| 2 | 7 | 64 | 5 | 69 | 76 | 10 | 86 |
| 3[3] | 1 | 72 | 13 | 85 | 67 | 19 | 86 |
| 3 | 2 | 76 | 10 | 86 | 74 | 15 | 89 |
| 3 | 3 | 77 | 9 | 86 | 77 | 14 | 91 |
| 3 | 4 | 76 | 8 | 84 | 78 | 13 | 91 |
| 3 | 5 | 75 | 8 | 83 | 76 | 12 | 88 |
| 3 | 6 | 75 | 6 | 81 | 80 | 9 | 89 |
| 3 | 7 | 74 | 6 | 80 | 79 | 10 | 89 |
| 3 | 8 | 73 | 7 | 80 | 77 | 11 | 88 |
| 3 | 9 | 73 | 6 | 79 | 79 | 11 | 91 |
| 3 | 10 | 71 | 6 | 77 | 80 | 10 | 90 |

[1] Freshly prepared catalyst as described.
[2] Catalyst burned clean in air and steam at 550° C.
[3] Catalyst burned clean in air and steam at 550° C.; soaked in 5.5 percent HCl at ~30° C. for 2 hours then washed with water.

EXAMPLE 5

This example illustrates the effectiveness of a treatment with aqueous nitric acid in promoting the lifetime of the catalyst.

A 50 milliliter portion of a steam treated tantalum oxidesilica gel catalyst contained in a tubular reactor is heated to 250°-265° C. in a nitrogen flow of 465 milliliters per minute and a solution of trioxane in isobutyric anhydride (1:3 on a molar basis) is vaporized and passed over the catalyst at a rate of about 65 milliliters of liquid feed per hour. The results of the run are summarized in Table IV (Run 1).

A second 50 milliliter portion of the same steam treated catalyst which has been similarly used in pivalolactone production is burned clean in a steam atmosphere at 550° C. by gradually replacing a nitrogen stream with air. Full steam and air are passed through the hot bed (550° C.) until the carbon deposits are removed and the catalyst appears clean visually. The catalyst is then cooled to ambient temperature under nitrogen.

The cleaned catalyst is then held in contact with 5 percent aqueous nitric acid for 2 hours at ambient temperature, washed with four 200milliliter portions of water, and dried at 260° C. in nitrogen.

The same feed composition as used in Run 1 is vaporized and fed over the catalyst at 250°-270° C. at a rate of about 62 milliliters of liquid feed per hour and with a nitrogen flow of 465 milliliters per minute. The results are shown in Table IV (Run 2).

The catalyst is burned clean as in Run 2 and contacted with 10 percent aqueous nitric acid for 2 hours

TABLE II

| Run No. | Hours of Operation | CH$_2$O Conversion to | | |
|---|---|---|---|---|
| | | PVL (%) | IBPVA (%) | Total (%) |
| (1) | 1 | 51 | 34 | 85 |
| | 7 | 63 | 22 | 85 |
| | 24 | 67 | 18 | 85 |
| | 31 | 66 | 17 | 83 |
| | 59 | 65 | 14 | 79 |
| (2) | 1 | 47 | 34 | 81 |
| | 7 | 56 | 27 | 83 |
| | 29 | 63 | 23 | 86 |
| | 50 | 63 | 19 | 82 |
| | 72 | 65 | 15 | 80 |
| | 79 | 65 | 14 | 79 |

(1) Freshly prepared catalyst as described
(2) Catalyst prepared and treated with 1.5 N aqueous HCl

TABLE III

| Run No. | Hours of Operation | CH$_2$O Conversion to | | |
|---|---|---|---|---|
| | | PVL (%) | IBPVA (%) | Total (%) |
| (1) | 1 | 51 | 11 | 62 |
| | 7 | 54 | 11 | 65 |
| | 23 | 40 | 11 | 51 |
| | 47 | 36 | 6 | 42 |
| | 53 | 30 | 6 | 36 |
| (2) | 1 | 42 | 11 | 53 |
| | 6 | 52 | 11 | 63 |
| | 24 | 50 | 11 | 61 |
| | 28 | 51 | 11 | 62 |
| (3) | 1 | 34 | 28 | 62 |
| | 7 | 44 | 26 | 70 |
| | 24 | 50 | 20 | 70 |
| | 48 | 48 | 12 | 60 |

TABLE III-continued

| Run No. | Hours of Operation | CH₂O Conversion to | | |
|---|---|---|---|---|
| | | PVL (%) | IBPVA (%) | Total (%) |
| | 70 | 50 | 7 | 57 |

[1] Fresh steam treated catalyst. [2] Catalyst after burning clean and treated with 1.5 N phosphoric acid at ambient temperature.
[3] Catalyst after burning clean and treated with 1.5 N phosphoric acid at 80–100° C.

TABLE IV

| Run No. | Days of Operation | CH₂O Conversion to | | | IBA Yield to | | |
|---|---|---|---|---|---|---|---|
| | | PVL (%) | IBPVA (%) | Total (%) | PVL (%) | IBPVA (%) | Total (%) |
| (1) | 1 | 67 | 16 | 83 | 66 | 24 | 90 |
| | 2 | 66 | 11 | 77 | 70 | 17 | 87 |
| | 3 | 63 | 10 | 73 | 74 | 18 | 92 |
| (2) | 1 | 67 | 15 | 82 | 64 | 22 | 86 |
| | 2 | 69 | 13 | 82 | 69 | 19 | 88 |
| | 3 | 70 | 11 | 81 | 72 | 18 | 90 |
| | 4 | 69 | 11 | 80 | 72 | 17 | 89 |
| | 5 | 70 | 11 | 81 | 72 | 17 | 89 |
| | 6 | 68 | 10 | 78 | 70 | 16 | 86 |
| | 7 | 66 | 10 | 76 | 71 | 17 | 88 |
| (3) | 1 | 70 | 15 | 85 | 65 | 22 | 87 |
| | 2 | 73 | 12 | 85 | 74 | 19 | 93 |
| | 3 | 73 | 11 | 84 | 76 | 17 | 93 |
| | 4 | 71 | 11 | 82 | 77 | 16 | 93 |

[1] Usual steam treated catalyst.
[2] Catalyst after burning clean and treatment with 5 percent nitric acid.
[3] Catalyst after burning clean and treatment with 10 percent nitric acid.

The invention has been described in detail with particular reference to preferred embodiments thereof, but it will be understood that variations and modifications can be effected within the spirit and scope of the invention as described hereinabove and in the appended claims.

I claim:

1. A process for producing a 2,2-disubstituted propiolactone having the formula

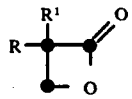

which comprises reacting an isoanhydride having the formula

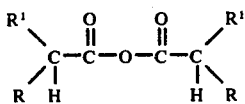

wherein R and R¹ individually may be straight- or branched-chain alkyl, aryl or aralkyl having 1 to 10 carbon atoms, with formaldehyde or a formaldehyde yielding material at a temperature of from about 190° C. to about 400° C., in the presence of a catalyst consisting of the acid treated metal oxide-silica gel complex which results from: (1) heating the calcined residue of a mixture of silica gel and a water-soluble salt of a metal selected from the group consisting of tantalum, titanium, niobium and zirconium to a temperature of from about 650° C. to about 1000° C. in the presence of water vapor, and (2) soaking the product of step (1) in a mineral acid.

2. The process of claim 1 wherein each R and R¹ individually is straight- or branched-chain alkyl of 1 to 6 carbon atoms.

3. The process of claim 1 wherein the isoanhydride is selected from the group consisting of isobutyric anhydride, 2-ethylhexanoic anhydride, 2-phenylpropionic anhydride, 2-ethylbutyric anhydride, and 2-methylpentanoic anhydride.

4. The process of claim 1 wherein the catalyst is formed by mixing a water-soluble salt of the selected heavy metal with silica gel, removing the water by evaporation, and subsequently calcining the material at a temperature of from about 400° C. to about 600° C.

5. The process of claim 4 wherein the calcining takes place at a temperature of from about 500° C. to about 550° C.

6. The process of claim 1 wherein the calcined residue is heated, in the presence of water vapor, to a temperature of from about 730° C. to about 780° C.

7. The process of claim 6 wherein the calcined residue is heated, in the presence of water vapor, for a period of from about 3 to about 6 hours.

8. The process of claim 6 wherein the calcined residue is heated, in the presence of water vapor, to a temperature of from about 760° C. to about 780° C.

9. The process of claim 8 wherein the calcined residue is heated, in the presence of water vapor, for a period of from about 4 to about 6 hours.

10. The process of claim 1 wherein the mineral acid is selected from the group consisting of HCl, HF, HBr, HNO₃, H₂SO₄ and H₃PO₄.

11. The process according to claim 10 wherein the mineral acid is utilized as an aqueous solution thereof.

12. A process according to claim 10 wherein the catalyst is soaked in the mineral acid for a period of from about 1 to about 4 hours at a temperature of from about 25° C. to about 100° C.

13. The process of claim 1 wherein the reaction is conducted at a temperature of from about 240° C. to about 300° C.

14. The process of claim 1 wherein the process is conducted at atmospheric pressure.

15. The process of claim 1 wherein the ratio of anhydride to aldehyde is from about 1.15 to 1 to about 5 to 1.

16. The process of claim 12 wherein the ratio of anhydride to aldehyde is from about 3 to 1 to about 4 to 1.

17. A process for producing pivalolactone which comprises reacting isobutyric anhydride and formaldehyde at a temperature of from about 190° C. to about 400° C. in the presence of a catalyst consisting of the acid treated metal oxide-silica gel complex which results from: (1) heating the calcined residue of a mixture of silica gel and a water-soluble salt of a metal selected from the group consisting of tantalum, titanium, niobium and zirconium to a temperature of from about 650° C. to about 1000° C. in the presence of vapor and (2) soaking the product of step (1) in a mineral acid.

18. The process of claim 17 wherein the catalyst is formed by mixing a water-soluble salt of the selected heavy metal with silica gel, removing the water by evaporation, and subsequently calcining the material at a temperature of from about 400° C. to about 550° C.

19. The process of claim 18 wherein the calcining takes place at a temperature of from about 500° C. to about 550° C.

20. The process of claim 17 wherein the calcined residue is heated, in the presence of water vapor, to a temperature of from about 730° C. to about 780° C.

21. The process of claim 20 wherein the calcined residue is heated, in the presence of water vapor, for a period of from about 3 to about 6 hours.

22. The process of claim 20 wherein the calcined residue is heated, in the presence of water vapor, to a temperature of from about 760° C. to about 780° C.

23. The process of claim 20 wherein the calcined residue is heated in the presence of water vapor for a period of from about 4 to about 6 hours.

24. The process of claim 17 wherein the mineral acid is selected from the group consisting of HCl, HF, HBr, $HNO_3$, $H_2SO_4$ and $H_3PO_4$.

25. The process according to claim 17 wherein the mineral acid is utilized as an aqueous solution thereof.

26. A process according to claim 17 wherein the catalyst is soaked in the mineral acid for a period of from about 1 to about 4 hours at a temperature of from about 25° C. to about 100° C.

27. The process of claim 17 wherein the reaction is conducted at a temperature of from about 240° C. to about 300° C.

28. The process of claim 17 wherein the reaction is conducted at atmospheric pressure.

29. The process of claim 17 wherein the ratio of anhydride fed to aldehyde is from about 1.15 to 1 to about 5 to 1.

30. The process of claim 29 wherein the ratio of anhydride fed to aldehyde is from about 3 to 1 to about 4 to 1.

* * * * *